United States Patent [19]
Wu et al.

[11] Patent Number: 6,106,527
[45] Date of Patent: Aug. 22, 2000

[54] VERTEBRAL FIXING DEVICE

[75] Inventors: Shing-Sheng Wu; Po-Quang Chen, both of Taipei, Taiwan

[73] Assignee: National Science Council, Taipei, Taiwan

[21] Appl. No.: 09/232,935

[22] Filed: Jan. 19, 1999

[51] Int. Cl.[7] .................................................. A61B 17/58
[52] U.S. Cl. ............................ 606/61; 606/57; 606/105; 623/17
[58] Field of Search ............................... 606/61, 57, 105; 623/17

[56] References Cited

U.S. PATENT DOCUMENTS

| | | | |
|---|---|---|---|
| 4,573,454 | 3/1986 | Hoffman | 606/61 |
| 5,681,312 | 10/1997 | Yuan et al. | 606/61 |
| 5,810,815 | 9/1998 | Morales | 606/61 |

*Primary Examiner*—Michael Buiz
*Assistant Examiner*—Julian W. Woo

[57] ABSTRACT

A vertebral fixing device for a patient having a diseased vertebral column segment for fastening a first vertebral column segment and a second vertebral column segment at both ends of the diseased vertebral column segment includes a first fixing piece having a first fixing medium integrally formed thereto and secured to the first vertebral column segment, and a second fixing piece having a second fixing medium integrally formed thereto and secured to the second vertebral column segment. The vertebral fixing device further includes a fixing unit having a first and a second hole respectively penetrating therethrough the two fixing mediums for fixing together the two fixing mediums.

19 Claims, 2 Drawing Sheets

VERTEBRAL FIXING DEVICE

FIELD OF THE INVENTION

The present invention relates to a fixing device, especially to a vertebral fixing device for a patient having a diseased vertebral column.

BACKGROUND OF THE INVENTION

Generally, the fixing method of the commonly used vertebral fixing device is not appropriate, that it is easily loosened from the vertebral column. Furthermore, the vertebral fixing device is not so strong that the patient needs a backboard to support the vertebral column or must apply a plaster to the body to fasten the vertebra column. Because the climate of Taiwan is hot and humid, the patient with a back board or a plaster will feel very uncomfortable it is also inconvenient for the patient to move. Besides, the surgeon must move the patient several times during the operation in order to install the vertebral fixing unit in the human body. The process of the surgical operation is also very complicated. So, it is desirable to improve the design of the vertebral fixing device.

SUMMARY OF THE INVENTION

An object of the present invention is to provide a vertebral fixing device for a patient having a diseased vertebral column for fastening the vertebral column.

According to the present invention, the vertebral fixing device for fastening a first vertebral column segment and a second vertebral column segment at both ends of the diseased vertebral column segment includes a first fixing piece having a first fixing medium integrally formed thereto and secured to the first vertebral column segment and a second fixing piece having a second fixing medium integrally formed thereto and secured to the second vertebral column segment.

In accordance with one aspect of the present invention, the first fixing piece includes a first channel provided in the first fixing piece for inserting thereinto the second fixing medium of the second fixing piece, a first fixing hole communicating with the first channel, and a first through hole communicating with the first channel.

In accordance with another aspect of the present invention, the first fixing piece is secured to the first vertebral column segment by a first screw.

In accordance with another aspect of the present invention, the first screw is a vertebral body screw passing through the first through hole.

In accordance with another aspect of the present invention, the first screw stops the second fixing medium sliding in the first channel.

In accordance with another aspect of the present invention, the first fixing piece further includes a first fixing screw passing through the first fixing hole to secure the second fixing medium in the first channel.

In accordance with another aspect of the present invention, the second fixing piece includes a second channel provided in the second fixing piece for inserting thereinto the first fixing medium of the first fixing piece, a second fixing hole communicating with the second channel, and a second through hole communicating with the second channel.

In accordance with another aspect of the present invention, the second fixing piece is secured to the second vertebral column segment by a second screw.

In accordance with another aspect of the present invention, the second screw is a vertebral body screw passing through the second through hole.

In accordance with another aspect of the present invention, the second screw stops the first fixing medium sliding in the second channel.

In accordance with another aspect of the present invention, the second fixing piece further includes a second fixing screw passing through the second fixing hole to secure the first fixing medium in the second channel In accordance with another aspect of the present invention, the vertebral fixing device further includes a fixing unit having a first and a second hole respectively penetrating therethrough the two fixing mediums for fixing together the two fixing mediums.

In accordance with another aspect of the present invention, the patient has a substitute for the diseased vertebral column segment.

In accordance with another aspect of the present invention, the fixing unit is secured to the substitute.

In accordance with another aspect of the present invention, the fixing unit includes the first hole provided in the fixing unit for penetrating therethrough the first fixing medium of the first fixing piece, the second hole provided in the fixing unit for penetrating therethrough the second fixing medium of the second fixing piece, a third through hole, a third fixing hole communicating with the first hole, and a fourth fixing hole communicating with the second hole.

In accordance with another aspect of the present invention, the fixing unit is secured to the substitute by a third screw passing through the third through hole.

In accordance with another aspect of the present invention, the fixing unit includes a third fixing screw passing through the third fixing hole for securing therewith the first fixing medium of the first fixing piece.

In accordance with another aspect of the present invention, the fixing unit includes a fourth fixing screw passing through the fourth fixing hole for securing therewith the second fixing medium of the second fixing piece.

In accordance with another aspect of the present invention, the vertebral fixing device further includes an additional fixing unit to be secured to the substitute.

In accordance with another aspect of the present invention, the vertebral fixing device is an anterior vertebral fixing device.

The present invention may best be understood through the following description with reference to the accompanying drawings, in which:

DETAILED DESCRIPTION OF THE PREFERRED EMBODIMENTS

Figure 1:
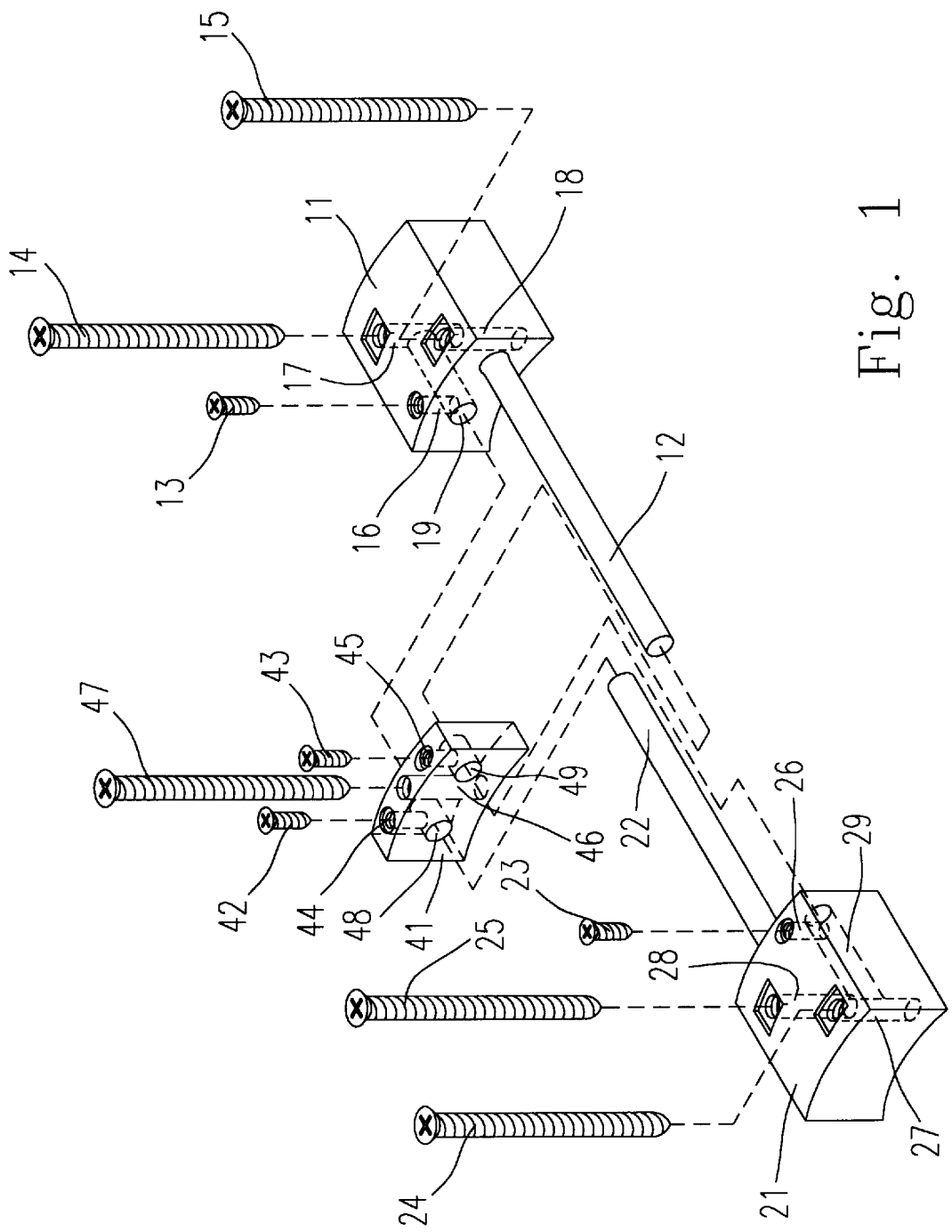
FIG. 1 is an exploded view showing how to assemble the vertebral fixing device according to the present invention.

Referring to FIG. 1, there are a first rod 12 integrally formed to the first plate 11 and a second rod 22 integrally formed to a second plate 21. A first channel 19 is provided in the first plate 11 for inserting thereinto the second rod 22. A short screw hole 16 and a long screw hole 17 are both communicated with the first channel 19. Two vertebral body screws 14, 15 pass through the long screw holes 17, 18 for securing the first plate 11. A short screw 13 passes through the first short screw hole 16 to secure the second rod 22 in the first channel 19.

A second channel 29 is provided in the second plate 21 for inserting thereinto the first rod 12. A short screw hole 26 and a long screw hole 27 are both communicated with the second channel 29. Two vertebral body screws 24, 25 pass through the long screw hole 27, 28 for securing the second plate 21. A short screw 23 passes through the second short screw hole 26 to secure the first rod 12 in the second channel 29.

In the vertebral fixing device, there is also a fixing unit 41 having a first hole 48 and a second hole 49 respectively penetrating therethrough the rods 22, 12 for fixing together the rods 22, 12. The fixing unit includes a long screw 47 passing through a long screw hole 46, a short screw hole 44 communicating with the first hole 48, a short screw 42 passing through the short screw hole 44 for securing therewith the second rod 22, a short screw hole 45 communicating with the second hole 49, and a short screw 43 passing through the short screw hole 45 for securing therewith the first rod 12.

Figure 2:
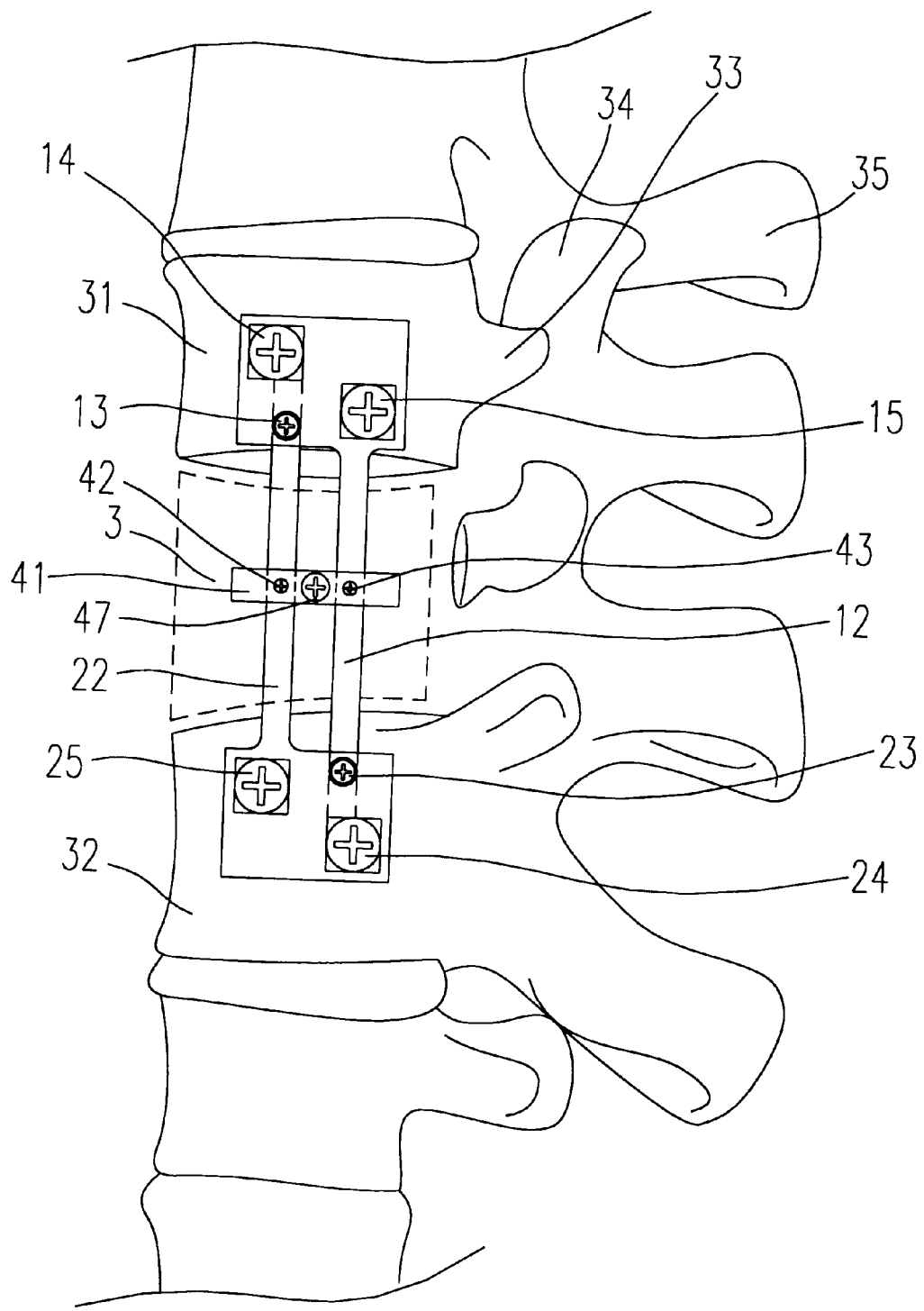
FIG. 2 is a schematic diagram showing the vertebral fixing device positioned on a diseased vertebra according to the present invention.

Referring to FIG. 2, there is a substitute 3 for the diseased vertebral column segment. The vertebral fixing unit is secured to a first vertebral column segment 31 and a second vertebral column segment 32 at both ends of the diseased vertebral column segment.

The first plate is secured to the first vertebral column segment 31 by the long screws 14, 15 and the second plate is secured to the second vertebral column segment 32 by the long screws 24, 25. The second rod 22 is secured to the first plate 11 by the short screw 13. When the second rod 22 slides in the first channel of the first plate, the long screw 14 can stop the second rod. At the same time, the first rod 12 is secured to the second plate 21 by the short screw 23. When the first rod 12 slides in the second channel of the second plate 21, the long screw 24 can stop the first rod.

The first rod 12 and the second rod 22 are respectively secured to the fixing unit 41 by the short screw 43 and the short screw 42. Finally, the fixing unit 41 is secured to the substitute 3 by the long screw 47. The vertebral fixing device includes an additional fixing unit to be secured to the substitute for fixing the vertebral column more tightly.

Therefore, the fixing method of this vertebral fixing device is appropriate and not easy to loosen. The vertebral fixing device is strong enough to fasten the vertebral column, so there is no need to use a backboard or apply a plaster for fixing the vertebral column. The patient will feel relatively comfortable and the process of the surgical operation will become more simple.

While the invention has been described in terms of what are presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A vertebral fixing device for being used with a patient having a diseased vertebral column segment and being fastened to a first vertebral column segment and a second vertebral column segment at both ends of said diseased vertebral column segment of said patient comprising:

a first fixing piece having a first fixing medium integrally formed thereto and adapted to be secured to said first vertebral column segment of said patient; and a second fixing piece having a second fixing medium integrally formed thereto and adapted to be secured to said second vertebral column segment of said patient, wherein said first fixing piece has a first channel for receiving said second fixing medium of said second fixing piece and said second fixing piece has a second channel for receiving said first fixing medium of said first fixing piece.

2. The device according to claim 1 wherein said first fixing piece further comprises:

a first fixing hole communicating with said first channel; and a first through hole communicating with said first channel.

3. The device according to claim 2 further comprising a first fixer adapted to be secured to said first vertebral column segment of said patient and wherein said first fixing piece engages with said first fixer and is secured to said first vertebral column segment of said patient by a first fixer.

4. The device according to claim 3 wherein said first fixer is a vertebral body screw passing through said first through hole.

5. The device according to claim 4 wherein said first fixer stops said second fixing medium sliding in said first channel.

6. The device according to claim 2 wherein said first fixing piece further comprises a first fastening unit passing through said first fixing hole to secure said second fixing medium in said first channel.

7. The device according to claim 2 wherein said second fixing piece further comprises:

a second fixing hole communicating with said second channel; and a second through hole communicating with said second channel.

8. The device according to claim 7 further comprising a second fixer adapted to be secured to said second vertebral column segment of said patient and wherein said second fixing piece engages with said second fixer and is secured to said second vertebral column segment of said patient by a second fixer.

9. The device according to claim 8 wherein said second fixer is a vertebral body screw passing through said second through hole.

10. The device according to claim 9 wherein said second fixer stops said first fixing medium sliding in said second channel.

11. The device according to claim 7 wherein said second fixing piece further comprises a second fastening unit passing through said second fixing hole to secure said first fixing medium in said second channel.

12. The device according to claim 1 wherein said vertebral fixing device further comprises a fixing unit having a first and a second hole that respectively penetrates said fixing unit to said first and second fixing mediums so as to fix together said first and second fixing mediums.

13. The device according to claim 12 wherein said fixing unit is adapted to be secured to a substitute which is mounted between said first vertebral column and said second vertebral column of said patient.

14. The device according to claim 12 wherein said fixing unit comprises:

said first hole provided in said fixing unit for penetrating said first fixing unit of said first fixing piece;

said second hole provided in said fixing unit for penetrating said second fixing unit of said second fixing piece;

a third through hole;

a third fixing hole communicating with said first hole; and a fourth fixing hole communicating with said second hole.

15. The device according to claim 14 wherein said fixing unit is secured to said substitute by a third fixer passing through said third through hole.

16. The device according to claim 14 wherein said fixing unit comprises a third fastening unit passing through said third fixing hole for securing therewith said first fixing medium.

17. The device according to claim 14 wherein said fixing unit comprises a fourth fasting unit passing through said fourth fixing hole for securing therewith said second fixing medium.

18. The device according to claim 14 wherein said vertebral fixing device further comprises an additional said fixing unit to be secured to said substitute.

19. The device according to claim 1 wherein said vertebral fixing device is an anterior vertebral fixing device.

* * * * *